United States Patent
Patel

(10) Patent No.: US 8,840,940 B2
(45) Date of Patent: Sep. 23, 2014

(54) KERATOLYTIC EMOLLIENT

(71) Applicant: Prugen IP Holdings, Inc., Scottsdale, AZ (US)

(72) Inventor: Bhiku G. Patel, Chandler, AZ (US)

(73) Assignee: PruGen IP Holdings, Inc., Scottsdale, AZ (US)

( * ) Notice: Subject to any disclaimer, the term of this patent is extended or adjusted under 35 U.S.C. 154(b) by 0 days.

(21) Appl. No.: 13/942,537

(22) Filed: Jul. 15, 2013

(65) Prior Publication Data

US 2014/0030367 A1   Jan. 30, 2014

Related U.S. Application Data

(60) Provisional application No. 61/671,564, filed on Jul. 13, 2012.

(51) Int. Cl.
| | | |
|---|---|---|
| *A61K 8/31* | (2006.01) | |
| *A61K 8/42* | (2006.01) | |
| *A61K 8/73* | (2006.01) | |
| *A61K 8/92* | (2006.01) | |
| *A61Q 19/00* | (2006.01) | |
| *A61Q 5/00* | (2006.01) | |
| *A61K 8/19* | (2006.01) | |
| *A61K 8/34* | (2006.01) | |

(52) U.S. Cl.
CPC ... *A61K 8/42* (2013.01); *A61K 8/92* (2013.01); *A61K 8/31* (2013.01); *A61Q 5/00* (2013.01); *A61K 8/73* (2013.01); *A61Q 19/00* (2013.01); *A61K 8/19* (2013.01); *A61K 8/733* (2013.01); *A61K 8/34* (2013.01)

USPC .......................................................... 424/769

(58) Field of Classification Search
None
See application file for complete search history.

(56) References Cited

U.S. PATENT DOCUMENTS

| | | | | |
|---|---|---|---|---|
| 2,881,161 | A * | 4/1959 | Kohler et al. ..................... 536/3 |
| 4,124,720 | A * | 11/1978 | Wenmaekers ................ 514/452 |
| 5,425,954 | A | 6/1995 | Thompson et al. |
| 5,449,519 | A | 9/1995 | Wolf et al. |
| 5,919,470 | A * | 7/1999 | Valdez et al. ................. 424/401 |
| 6,503,492 | B2 * | 1/2003 | McGlone et al. ............... 424/65 |
| 6,986,896 | B2 * | 1/2006 | Bhagwat et al. ............. 424/401 |
| 2002/0085982 | A1 * | 7/2002 | Dorf ............................... 424/63 |
| 2003/0165577 | A1 | 9/2003 | Bhagwat et al. |
| 2006/0013788 | A1 | 1/2006 | Filippi |
| 2007/0098647 | A1 * | 5/2007 | Neubourg ....................... 424/47 |
| 2011/0067867 | A1 | 3/2011 | Reddy et al. |

OTHER PUBLICATIONS

Lee et al. (Abstract of: Wound Repair Regen. 2009, 17(4):505-10) as evidenced by CARMOL® 40 ([online] retrieved on Oct. 30, 2013 from: http://dailymed.nlm.nih.gov/dailymed/archives/fdaDrugInfo.cfm?archiveid=78076; 9 pages).*
CARMOL® 40 ([online] retrieved on Oct. 30, 2013 from: http://dailymed.nlm.nih.gov/dailymed/archives/fdaDrugInfo.cfm?archiveid=78076; 9 pages).*
PCT/US2013/050556—International Search Report and Written Opinion dated Oct. 6, 2013.

* cited by examiner

*Primary Examiner* — Ernst V Arnold
(74) *Attorney, Agent, or Firm* — Dale F. Regelman; Quarles & Brady LLP

(57) ABSTRACT

A keratolytic emollient, which includes urea, mineral oil, and paraffin wax.

19 Claims, 6 Drawing Sheets

FIG. 2A

| COMPOUND | A | B | C | D |
|---|---|---|---|---|
| UREA | 40 | 40 | 40 | 40 |
| MINERAL OIL | 5 | 5 | 5 | 5 |
| PARAFFIN WAX | 1.5 | 1.5 | 1.5 | 1.5 |
| CETYL PALMITATE | 1 | 4 | 7 | 10 |
| AVACADO OIL | 1 | 6 | 6 | 6 |
| ETHYLENE GLYCOL MONOSTEARATE | 6 | 6 | 6 | 6 |
| GLYCERIN | 2 | 5 | 10 | 15 |
| TRIETHANOLAMMONIUM ALGINATE | 1 | 3 | 4 | 5 |
| SODIUM ALGINATE | 1 | 4 | 7 | 10 |
| SHEA BUTTER | 0 | 0.5 | 1 | 1.5 |
| SQUALANE | 1 | 3 | 4 | 5 |
| PALMITAMIDE MEA | 0.5 | 0.5 | 0.5 | 0.5 |
| STEARIC ACID | 3 | 0.5 | 0.5 | 0.5 |
| TRIETHANOLAMINE | 7 | 7 | 7 | 7 |

FIG. 2B

| COMPOUND | A | B | C | D |
|---|---|---|---|---|
| TRIETHANOLAMMONIUM GULURONATE | 0 | 1 | 3 | 4 |
| SODIUM GULURONATE | 0 | 1 | 4 | 7 |
| DIETHANOLAMINE GULURONAMIDE | 0 | 0.5 | 1 | 1.5 |
| TRIETHANOLAMMONIUM MANURONATE | 0 | 1 | 3 | 4 |
| SODIUM MANURONATE | 0 | 1 | 4 | 7 |
| DIETHANOLAMINE MANURONAMIDE | 0 | 0.5 | 1.0 | 1.5 |
| DIETHANOLAMINE ALGINAMIDE | 0 | 0.5 | 1.0 | 1.5 |

FIG. 3

| COMPOUND | E | F | G | H | I | J | K | L | M | N | O | P | Q |
|---|---|---|---|---|---|---|---|---|---|---|---|---|---|
| SODIUM ALGINATE | 0.25 | 0.50 | 0.75 | 0.25 | 0.50 | 0.75 | 0.25 | 0.50 | 0.75 | 0.25 | 0.50 | 0.75 | 0.00 |
| PALMITAMIDE MEA | 0.10 | 0.10 | 0.10 | 0.75 | 0.75 | 0.75 | 0.50 | 0.50 | 0.50 | 0.00 | 0.50 | 0.50 | 0.50 |
| TRIETHANOLAMINE ALGINATE | 0.70 | 0.70 | 0.70 | 0.70 | 0.70 | 0.70 | 0.70 | 0.70 | 0.70 | 0.70 | 0.70 | 0.70 | 0.70 |

FIG. 4

| COMPOUND | AR | AS | AT | AU | AV | AW | AX | AY | AZ | BA | BB | BC | BD |
|---|---|---|---|---|---|---|---|---|---|---|---|---|---|
| SODIUM ALGINATE | 0.25 | 0.50 | 0.75 | 0.25 | 0.50 | 0.75 | 0.25 | 0.50 | 0.75 | 0.25 | 0.50 | 0.75 | 0.00 |
| PALMITAMIDE MEA | 0.10 | 0.10 | 0.10 | 0.75 | 0.75 | 0.75 | 0.50 | 0.50 | 0.50 | 0.00 | 0.50 | 0.50 | 0.50 |
| SHEA BUTTER | 0.50 | 0.50 | 0.50 | 1.00 | 1.00 | 1.00 | 1.50 | 1.50 | 1.50 | 1.00 | 1.00 | 1.00 | 1.00 |
| TRIETHANOLAMINE ALGINATE | 0.70 | 0.70 | 0.70 | 0.70 | 0.70 | 0.70 | 0.70 | 0.70 | 0.70 | 0.70 | 0.70 | 0.70 | 0.70 |

FIG. 5

| COMPOUND | R | S | T | U | V | W | X | Y | Z | AA | AB | AC | AD |
|---|---|---|---|---|---|---|---|---|---|---|---|---|---|
| SODIUM ALGINATE | 0.25 | 0.50 | 0.75 | 0.25 | 0.50 | 0.75 | 0.25 | 0.50 | 0.75 | 0.25 | 0.50 | 0.75 | 0.00 |
| POLYMANURONIC ACID | 0.25 | 0.25 | 0.25 | 0.50 | 0.50 | 0.50 | 0.75 | 0.75 | 0.75 | 0.25 | 0.50 | 0.75 | 5.00 |
| PALMITAMIDE MEA | 0.10 | 0.10 | 0.10 | 0.75 | 0.75 | 0.75 | 0.50 | 0.50 | 0.50 | 0.00 | 0.50 | 0.50 | 0.50 |
| TRIETHANOLAMINE ALGINATE | 0.70 | 0.70 | 0.70 | 0.70 | 0.70 | 0.70 | 0.70 | 0.70 | 0.70 | 0.70 | 0.70 | 0.70 | 0.70 |

FIG. 6

| COMPOUND | AE | AF | AG | AH | AI | AJ | AK | AL | AM | AN | AO | AP | AQ |
|---|---|---|---|---|---|---|---|---|---|---|---|---|---|
| SODIUM ALGINATE | 0.25 | 0.50 | 0.75 | 0.25 | 0.50 | 0.75 | 0.25 | 0.50 | 0.75 | 0.25 | 0.50 | 0.75 | 0.00 |
| POLYGULURONIC ACID | 0.25 | 0.25 | 0.25 | 0.50 | 0.50 | 0.50 | 0.75 | 0.75 | 0.75 | 0.25 | 0.50 | 0.75 | 5.00 |
| PALMITAMIDE MEA | 0.10 | 0.10 | 0.10 | 0.75 | 0.75 | 0.75 | 0.50 | 0.50 | 0.50 | 0.00 | 0.50 | 0.50 | 0.50 |
| TRIETHANOLAMINE ALGINATE | 0.70 | 0.70 | 0.70 | 0.70 | 0.70 | 0.70 | 0.70 | 0.70 | 0.70 | 0.70 | 0.70 | 0.70 | 0.70 |

FIG. 7

| COMPOUND | BE | BF | BG | BH | BI | BJ | BK | BL | BM | BN | BO | BP | BQ |
|---|---|---|---|---|---|---|---|---|---|---|---|---|---|
| SODIUM ALGINATE | 0.10 | 0.30 | 0.50 | 0.70 | 0.90 | 1.00 | 0.10 | 0.30 | 0.50 | 0.70 | 0.90 | 1.00 | 0.00 |
| TRIETHANOLAMINE ALGINATE | 0.10 | 0.10 | 0.10 | 0.10 | 0.10 | 0.10 | 0.30 | 0.30 | 0.30 | 0.30 | 0.30 | 0.30 | 1.00 |

FIG. 8

| COMPOUND | BR | BS | BT | BU | BV | BW | BX | BY | BZ | CA | CB | CC | CD |
|---|---|---|---|---|---|---|---|---|---|---|---|---|---|
| SODIUM ALGINATE | 0.10 | 0.30 | 0.50 | 0.70 | 0.90 | 1.00 | 0.10 | 0.30 | 0.50 | 0.70 | 0.90 | 1.00 | 0.00 |
| TRIETHANOLAMINE ALGINATE | 0.50 | 0.50 | 0.50 | 0.50 | 0.50 | 0.50 | 0.70 | 0.70 | 0.70 | 0.70 | 0.70 | 0.70 | 1.00 |

FIG. 9

| COMPOUND | CE | CF | CG | CH | CI | CJ | CK | CL | CM | CN | CO | CP | CQ |
|---|---|---|---|---|---|---|---|---|---|---|---|---|---|
| SODIUM ALGINATE | 0.10 | 0.30 | 0.50 | 0.70 | 0.90 | 1.00 | 0.10 | 0.30 | 0.50 | 0.70 | 0.90 | 1.00 | 1.00 |
| TRIETHANOLAMINE ALGINATE | 0.90 | 0.90 | 0.90 | 0.90 | 0.90 | 0.90 | 1.00 | 1.00 | 1.00 | 1.00 | 1.00 | 0.90 | 1.00 |

KERATOLYTIC EMOLLIENT

CROSS REFERENCE TO RELATED APPLICATIONS

This U.S. Non-Provisional Application claims priority to a U.S. Provisional Application having Ser. No. 61/671,564 filed on Jul. 13, 2012, which is hereby incorporated by reference.

FIELD OF THE INVENTION

This invention is directed to keratolytic emollients for use on the skin or animals, including humans.

BACKGROUND OF THE INVENTION

Prior art urea creams have been used for debridement and promotion of normal healing of skin areas with hyperkeratosis, particularly where healing is inhibited by local skin infection, skin necrosis, fibrinous or itching debris or eschar. These prior art formulations include compounds labile to oxidation.

SUMMARY OF THE INVENTION

A keratolytic emollient is presented. In certain embodiments, Applicant's keratolytic emollient comprises urea, mineral oil, and paraffin wax. In certain embodiments, Applicant's keratolytic emollient does not comprise any compounds having one or more carbon-carbon double bonds.

BRIEF DESCRIPTION OF THE DRAWINGS

The invention will be better understood from a reading of the following detailed description taken in conjunction with the drawings in which like reference designators are used to designate like elements, and in which:

FIGS. 2A, 2B, 3, 4, 5, 6, 7, 8, and 9 recite various formulations of Applicant's keratolytic composition.

DETAILED DESCRIPTION OF PREFERRED EMBODIMENTS

Figure 1:
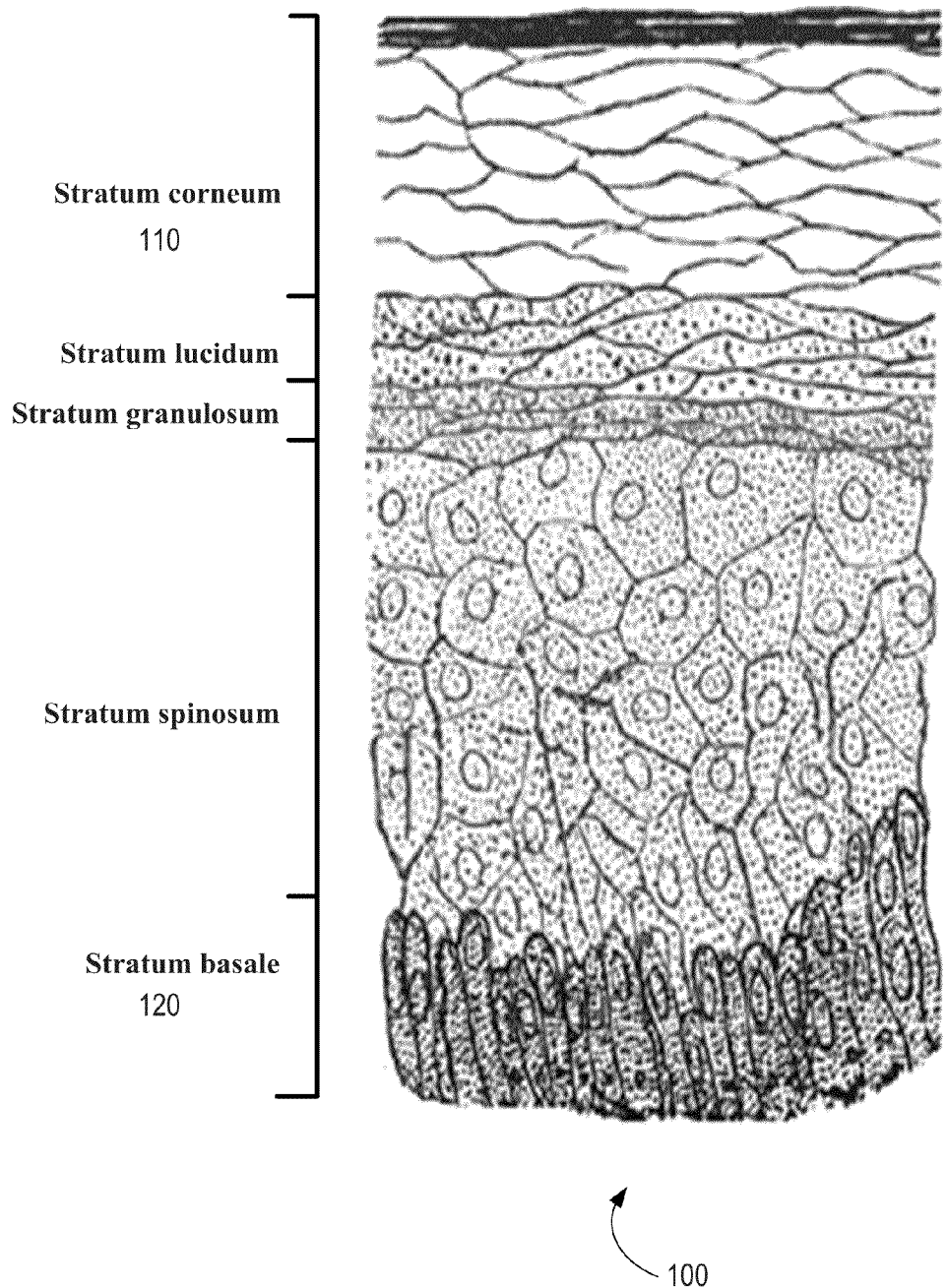
FIG. 1 illustrates the layers of the epidermis.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Referring now to FIG. 1, the stratum corneum 110 (Latin for 'horned layer') is the outermost layer of the epidermis 100, consisting of dead cells (corneocytes) that lack nuclei and organelles.

The purpose of the stratum corneum is to form a barrier to protect underlying tissue from infection, dehydration, chemicals and mechanical stress. Desquamation, the process of cell shedding from the surface of the stratum corneum, balances proliferating keratinocytes that form in the stratum basale 120. These cells migrate through the epidermis towards the surface in a journey that takes approximately fourteen days.

During cornification, the process whereby living keratinocytes are transformed into non-living corneocytes, the cell membrane is replaced by a layer of ceramides which become covalently linked to an envelope of structural proteins (the cornified envelope). This complex surrounds cells in the stratum corneum and contributes to the skin's barrier function. Corneodesmosomes (modified desmosomes) facilitate cellular adhesion by linking adjacent cells within this epidermal layer. These complexes are degraded by proteases, eventually permitting cells to be shed at the surface. Desquamation and formation of the cornified envelope are both required for the maintenance of skin homeostasis. A failure to correctly regulate these processes leads to the development of skin disorders.

The thickness of the stratum corneum varies throughout the body. In the palms of the hands and the soles of the feet this layer is typically thicker, since these regions require additional protection in order to grasp objects and avoid injury. In general, the stratum corneum contains 15 to 20 layers of dead cells. The stratum corneum has a thickness between 10 and 40 μm.

Cells of the stratum corneum contain a dense network of keratin, a protein that helps keep the skin hydrated by preventing water evaporation. These cells can also absorb water, further aiding in hydration, and explaining why humans and other animals experience wrinkling of the skin on the fingers and toes ("pruning") when immersed in water for prolonged periods. In addition, this layer is responsible for the "spring back" or stretchy properties of skin. A weak glutenous protein bond pulls the skin back to its natural shape.

Applicant's topical composition is a potent keratolytic emollient. In certain embodiments, Applicant's topical composition comprises about 30 weight percent urea, Compound 1. In certain embodiments, Applicant's topical composition comprises about 35 weight percent urea. In certain embodiments, Applicant's topical composition comprises about 40 weight percent urea. In certain embodiments for nail use, Applicant's topical composition comprises about 50 weight percent urea.

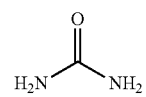

1

As those skilled in the art will appreciate, the terms urea and carbamide refer to a genus of chemical compounds comprising a structure RR'N—CO—NRR', wherein R and R' are independently selected from the group consisting of H, alkyl, alkenyl, and phenyl.

Applicant's keratolytic emollient functions as a debriding agent by accelerating the breakdown of dead skin and pus, which helps to loosen and shed hard and scaly skin. Urea dissolves the intercellular matrix of the cells of the stratum corneum, promoting desquamation of scaly skin, eventually resulting in softening of hyperkeratotic areas. In particular, aqueous solutions of urea dissolve keratin.

In certain embodiments, Applicant's keratolytic emollient comprises polymanuronic acid II wherein (n) is between about 10 and about 100.

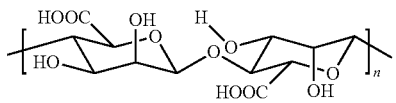

II

In certain embodiments, Applicant's keratolytic emollient comprises polymanuronic acid at about a 0.5 weight percent loading. In certain embodiments, Applicant's keratolytic emollient comprises polymanuronic acid at about a 0.75 weight percent loading. In certain embodiments, Applicant's keratolytic emollient comprises polymanuronic acid at about a 1 weight percent loading. In certain embodiments, Applicant's keratolytic emollient comprises polymanuronic acid at about a 1.25 weight percent loading. In certain embodiments, Applicant's keratolytic emollient comprises polymanuronic acid at about a 1.5 weight percent loading.

In certain embodiments, Applicant's keratolytic emollient comprises polymanuronic acid salt III wherein (n) is between about 10 and about 100.

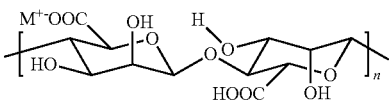

III

In certain embodiments, Applicant's keratolytic emollient comprises polymanuronic acid salt at about a 0.5 weight percent loading. In certain embodiments, Applicant's keratolytic emollient comprises polymanuronic acid salt at about a 0.75 weight percent loading. In certain embodiments, Applicant's keratolytic emollient comprises polymanuronic acid salt at about a 1 weight percent loading. In certain embodiments, Applicant's keratolytic emollient comprises polymanuronic acid salt at about a 1.25 weight percent loading. In certain embodiments, Applicant's keratolytic emollient comprises polymanuronic acid salt at about a 1.5 weight percent loading.

In certain embodiments, $M^+$ comprises one or more cations selected from the group consisting of sodium, potassium, ammonium, and triethanolammonium. In certain embodiments, $M^+$ comprises a monovalent moiety. In certain embodiments, $M^+$ does not comprise a polyvanent moiety. In certain embodiments, $M^+$ does not comprise a divalent moiety. In certain embodiments, M does not comprise a trivalent moiety.

In certain embodiments, about 25 percent of the —COOH groups comprising polymanuronic acid II have been converted to an acid salt. In certain embodiments, about 30 percent of the —COOH groups comprising polymanuronic acid II have been converted to an acid salt. In certain embodiments, about 35 percent of the —COOH groups comprising polymanuronic acid II have been converted to an acid salt. In certain embodiments, about 40 percent of the —COOH groups comprising polymanuronic acid II have been converted to an acid salt. In certain embodiments, about 45 percent of the —COOH groups comprising polymanuronic acid have been converted to an acid salt. In certain embodiments, about 50 percent of the —COOH groups comprising polymanuronic acid II have been converted to an acid salt.

In certain embodiments, Applicant's keratolytic emollient comprises polymanuronic amide XIII, formed by reaction of diethanol amine with polymanuronic acid, at about a 0.5 weight percent loading. In certain embodiments, Applicant's keratolytic emollient comprises polymanuronic amide XI at about a 0.75 weight percent loading. In certain embodiments, Applicant's keratolytic emollient comprises polymanuronic amide XI at about a 1 weight percent loading. In certain embodiments, Applicant's keratolytic emollient comprises polymanuronic amide XI at about a 1.25 weight percent loading. In certain embodiments, Applicant's keratolytic emollient comprises polymanuronic amide XI at about a 1.5 weight percent loading.

XIII

In certain embodiments, about 25 percent of the —COOH groups comprising polymanuronic acid II have been converted to the amide of diethanol amine. In certain embodiments, about 30 percent of the —COOH groups comprising polymanuronic acid II have been converted to the amide of diethanol amine. In certain embodiments, about 35 percent of the —COOH groups comprising polymanuronic acid II have been converted to the amide of diethanol amine. In certain embodiments, about 40 percent of the —COOH groups comprising polymanuronic acid II have been converted to the amide of diethanol amine. In certain embodiments, about 45 percent of the —COOH groups comprising polymanuronic acid II have been converted to the amide of diethanol amine. In certain embodiments, about 50 percent of the —COOH groups comprising polymanuronic acid II have been converted to the amide of diethanol amine.

In certain embodiments, Applicant's keratolytic emollient comprises polyguluronic acid, Compound IV wherein (n) is between about 10 and about 100.

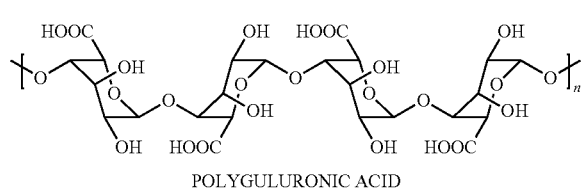

IV

POLYGULURONIC ACID

In certain embodiments, Applicant's keratolytic emollient comprises polyguluronic acid IV at about a 0.5 weight percent loading. In certain embodiments, Applicant's keratolytic emollient comprises polyguluronic acid at about a 0.75 weight percent loading. In certain embodiments, Applicant's keratolytic emollient comprises polyguluronic acid at about a 1 weight percent loading. In certain embodiments, Applicant's keratolytic emollient comprises polyguluronic acid at about a 1.25 weight percent loading. In certain embodiments, Applicant's keratolytic emollient comprises polyguluronic acid at about a 1.5 weight percent loading.

In certain embodiments, Applicant's keratolytic emollient comprises polyguluronic acid salt, Compound V wherein (n) is between about 10 and about 100.

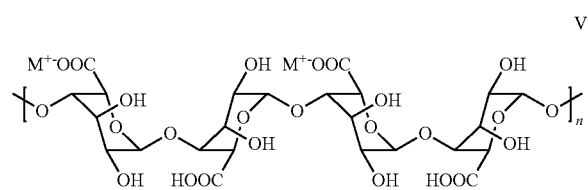

V

In certain embodiments, Applicant's keratolytic emollient comprises polyguluronic acid salt V at about a 0.5 weight percent loading. In certain embodiments, Applicant's keratolytic emollient comprises polyguluronic acid salt at about a 0.75 weight percent loading. In certain embodiments, Applicant's keratolytic emollient comprises polyguluronic acid salt at about a 1 weight percent loading. In certain embodiments, Applicant's keratolytic emollient comprises polyguluronic acid salt at about a 1.25 weight percent loading. In certain embodiments, Applicant's keratolytic emollient comprises polyguluronic acid salt at about a 1.5 weight percent loading.

In certain embodiments, M+ comprises one or more cations selected from the group consisting of sodium, potassium, ammonium, and triethanolammonium. In certain embodiments, M+ comprises a monovalent moiety. In certain embodiments, M+ does not comprise a polyvanent moiety. In certain embodiments, M+ does not comprise a divalent moiety. In certain embodiments, M+ does not comprise a trivalent moiety.

In certain embodiments, about 25 percent of the —COOH groups comprising polyguluronic acid. IV have been converted to an acid salt. In certain embodiments, about 30 percent of the —COOH groups comprising polyguluronic acid IV have been converted to an acid salt. In certain embodiments, about 35 percent of the —COOH groups comprising polyguluronic acid IV have been converted to an acid salt. In certain embodiments, about 40 percent of the —COOH groups comprising polyguluronic acid IV have been converted to an acid salt. In certain embodiments, about 45 percent of the —COOH groups comprising polyguluronic acid IV I have been converted to an acid salt. In certain embodiments, about 50 percent of the —COOH groups comprising polyguluronic acid IV have been converted to an acid salt.

In certain embodiments, Applicant's keratolytic emollient comprises polyguluronic amide XIV, formed by reaction of diethanol amine with polyguluronic acid, at about a 0.5 weight percent loading. In certain embodiments, Applicant's keratolytic emollient comprises polyguluronic amide XII at about a 0.75 weight percent loading. In certain embodiments, Applicant's keratolytic emollient comprises polyguluronic amide XII at about a 1 weight percent loading. In certain embodiments, Applicant's keratolytic emollient comprises polyguluronic amide XII at about a 1.25 weight percent loading. In certain embodiments, Applicant's keratolytic emollient comprises polyguluronic amide XII at about a 1.5 weight percent loading.

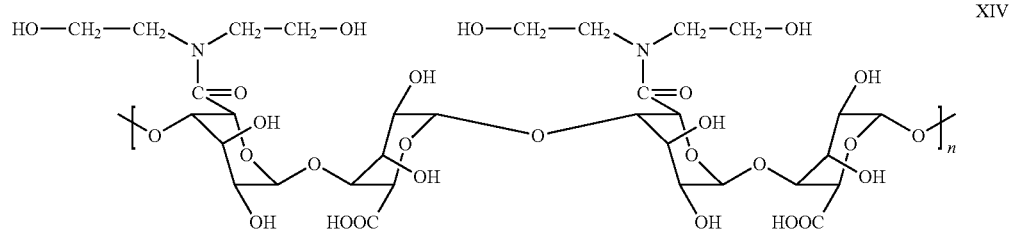

XIV

In certain embodiments, about 25 percent of the —COOH groups disposed in polyguluronic acid IV have been converted to the amide of diethanol amine. In certain embodiments, about 30 percent of the —COOH groups disposed in polyguluronic acid. IV have been converted to the amide of diethanol amine. In certain embodiments, about 35 percent of the —COOH groups disposed in polyguluronic acid IV have been converted to the amide of diethanol amine. In certain embodiments, about 40 percent of the —COOH groups disposed in polyguluronic acid IV have been converted to the amide of diethanol amine. In certain embodiments, about 45 percent of the —COOH groups disposed in polyguluronic acid IV have been converted to the amide of diethanol amine. In certain embodiments, about 50 percent of the —COOH groups disposed in polyguluronic acid IV have been converted to the amide of diethanol amine.

In certain embodiments, Applicant's keratolytic emollient comprises alginic acid XI wherein (n) is between about 10 and about 100, and wherein (m) is between about 10 and about 100.

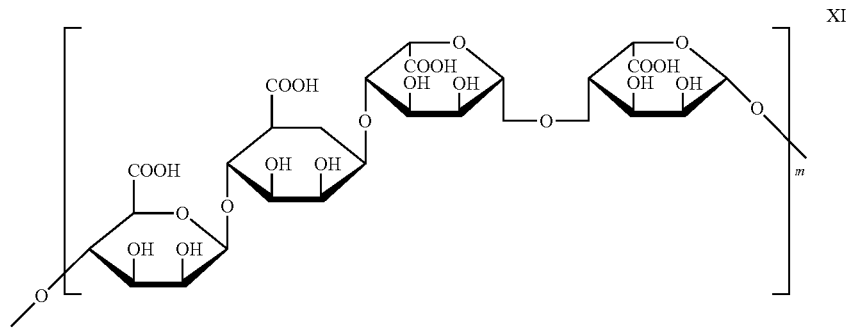

XI

In certain embodiments, Applicant's keratolytic emollient comprises alginic acid at about a 0.5 weight percent loading. In certain embodiments, Applicant's keratolytic emollient comprises alginic acid at about a 0.75 weight percent loading. In certain embodiments, Applicant's keratolytic emollient comprises alginic acid at about a 1 weight percent loading. In certain embodiments, Applicant's keratolytic emollient comprises alginic acid at about a 1.25 weight percent loading. In certain embodiments, Applicant's keratolytic emollient comprises alginic acid at about a 1.5 weight percent loading.

In certain embodiments, Applicant's keratolytic emollient comprises alginic acid salt XII wherein (n) is between about 10 and about 100, and wherein (m) is between about 10 and about 100.

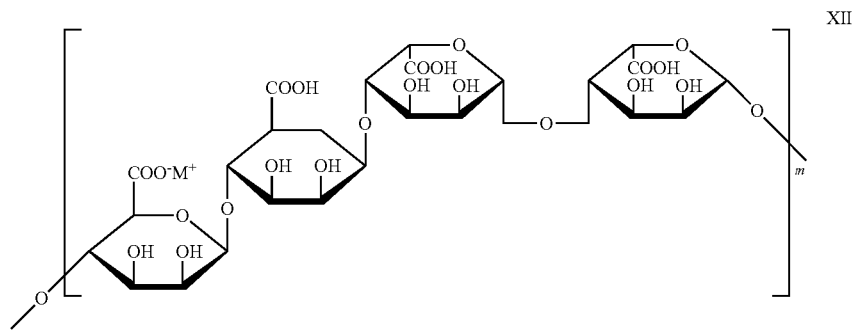

XII

In certain embodiments, Applicant's keratolytic emollient comprises alginic acid salt at about a 0.5 weight percent loading. In certain embodiments, Applicant's keratolytic emollient comprises alginic acid salt at about a 0.75 weight percent loading. In certain embodiments, Applicant's keratolytic emollient comprises alginic acid salt at about a 1 weight percent loading. In certain embodiments, Applicant's keratolytic emollient comprises alginic acid salt at about a 1.25 weight percent loading. In certain embodiments, Applicant's keratolytic emollient comprises alginic acid salt at about a 1.5 weight percent loading.

In certain embodiments, M+ comprises one or more cations selected from the group consisting of sodium, potassium, ammonium, and triethanolammonium. In certain embodiments, M+ comprises a monovalent moiety. In certain embodiments, M+ does not comprise a polyvanent moiety. In certain embodiments, M+ does not comprise a divalent moiety. In certain embodiments, M+ does not comprise a trivalent moiety.

In certain embodiments, about 25 percent of the —COOH groups comprising alginic acid XII have been converted to an acid salt. In certain embodiments, about 30 percent of the —COOH groups comprising alginic acid XII have been converted to an acid salt. In certain embodiments, about 35 percent of the —COOH groups comprising alginic acid XII have been converted to an acid salt. In certain embodiments, about 40 percent of the —COOH groups comprising alginic acid XII have been converted to an acid salt. In certain embodiments, about 45 percent of the —COOH groups comprising alginic acid XII have been converted to an acid salt. In certain embodiments, about 50 percent of the —COOH groups comprising alginic acid XII have been converted to an acid salt.

With regard to the use of anionic polysaccharides, such as for example polyguluronic acid salts V, and/or polymanuronic acid salts III, in certain embodiments smaller molecular weight compounds are favored over larger molecular weight compounds. In certain of these embodiments, (n) for salts III and V is about 10. In certain of these embodiments, Applicant's keratolytic composition comprises polyguluronic acid salts V having a number average molecular weight of about 5000 Daltons, wherein $M^+$ is selected from the group consisting of $Li^+$, $Na^+$, $K^+$, ammonium, and triethanolammonium, and wherein $M^+$ does not comprise a divalent cation or a trivalent cation or a tetravalent cation. In certain of these embodiments, Applicant's keratolytic composition comprises polymanuronic acid salts III having a number average molecular weight of about 5000 Daltons, wherein $M^+$ selected from the group consisting of $Li^+$, $Na^+$, $K^+$, ammonium, and triethanolammonium, and wherein $M^+$ does not comprise a divalent cation or a trivalent cation or a tetravalent cation.

With regard to the use of anionic polysaccharides, such as for example alginic acid salts XIII, in certain embodiments smaller molecular weight compounds are favored over larger molecular weight compounds. In certain of these embodiments, (n) is about 5 and (m) is about 5. In certain of these embodiments, Applicant's keratolytic composition comprises alginic acid salts XIII having a number average molecular weight of about 5000 Daltons, wherein M⁻ is selected from the group consisting of Li⁺, Na⁺, K⁺, ammonium, and triethanolammonium, and wherein M⁺ does not comprise a divalent cation or a trivalent cation or a tetravalent cation.

In certain embodiments, Applicant's keratolytic emollient comprises alginic amide XV, formed by reaction of diethanolamine with alginic acid, at about a 0.5 weight percent loading. In certain embodiments, Applicant's keratolytic emollient comprises alginic amide XV at about a 0.75 weight percent loading. In certain embodiments, Applicant's keratolytic emollient comprises alginic amide XV at about a 1 weight percent loading. In certain embodiments, Applicant's keratolytic emollient comprises alginic amide XV at about a 1.25 weight percent loading. In certain embodiments, Applicant's keratolytic emollient comprises alginic amide XV at about a 1.5 weight percent loading.

In certain embodiments, Applicant's keratolytic emollient comprises shea butter, Compound VII, at between about 1 to about 2 weight percent. Shea butter is a slightly yellowish or ivory-colored fat extracted from the nut of the African shea tree (*Vitellaria paradoxa*). Shea butter is a triglyceride (fat) derived mainly from stearic acid and oleic acid.

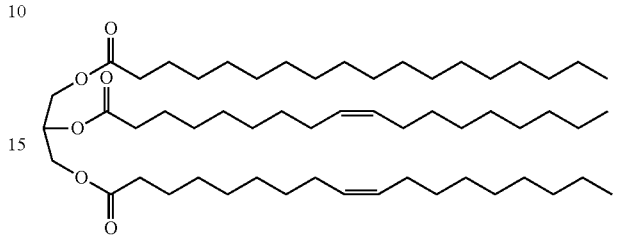

VII

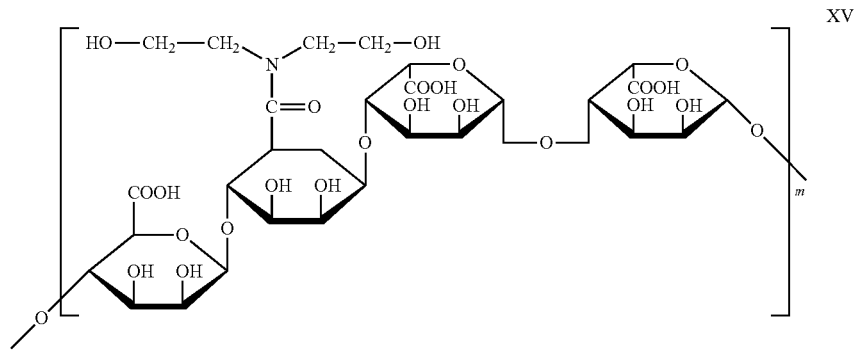

XV

In certain embodiments, about 25 percent of the —COOH groups disposed in alginic acid XII have been converted to the amide of diethanol amine. In certain embodiments, about 30 percent of the —COOH groups disposed in alginic acid XII have been converted to the amide of diethanol amine. In certain embodiments, about 35 percent of the —COOH groups disposed in alginic acid XII have been converted to the amide of diethanol amine. In certain embodiments, about 40 percent of the —COOH groups disposed in alginic acid XII have been converted to the amide of diethanol amine. In certain embodiments, about 45 percent of the —COOH groups disposed in alginic acid XII have been converted to the amide of diethanol amine. In certain embodiments, about 50 percent of the —COOH groups disposed in alginic acid XII have been converted to the amide of diethanol amine.

In certain embodiments, Applicant's keratolytic emollient comprises squalane, Compound VI, at between about 0.5 to about 2 weight percent. Squalane is a natural hydrocarbon and triterpene. It is a component of human sebum. Squalane is a saturated analog of squalene, from which it can also be produced by hydrogenation.

In certain embodiments, Applicant's keratolytic emollient comprises stearic acid at between about 2 to about 4 weight percent. Stearic acid is a saturated fatty acid with an 18 carbon chain and has the IUPAC name octadecanoic acid. It is a waxy solid, and its chemical formula is $CH_3(CH_2)_{16}CO_2H$.

In certain embodiments, Applicant's keratolytic emollient comprises cetyl palmitate, Compound VIII, at between about 0.5 to about 2 weight percent. Cetyl palmitate is the ester derived from palmitic acid and cetyl alcohol. It is the primary constituent of spermaceti, the wax found in the skull of sperm whales

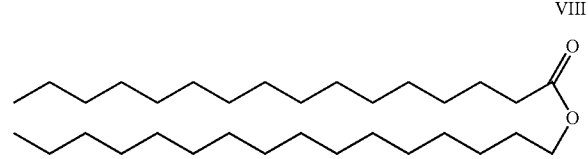 [SMILES: CCCCCCCCCCCCCCCCOC(=O)CCCCCCCCCCCCCCC]

VIII

VI

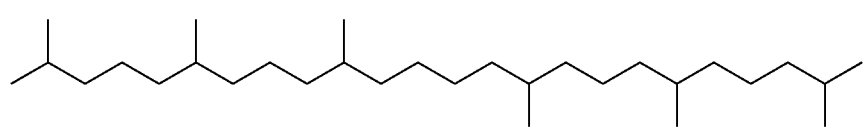

In certain embodiments, Applicant's keratolytic emollient comprises ethylene glycol monostearate, Compound IX, at between about 3 to about 9 weight percent.

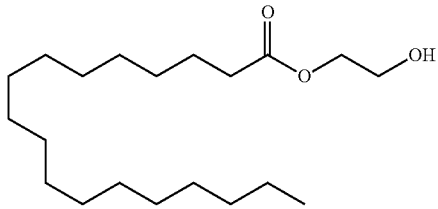

In certain embodiments, Applicant's keratolytic emollient comprises Palmitoylethanolamide, Compound X, at between about 0.25 to about 1 weight percent. Palmitoylethanolamide (PEA) is an endogenous fatty acid amide, belonging to the class of endocannabinoids. PEA has been demonstrated to bind to a receptor in the cell-nucleus (a nuclear receptor) and exerts a great variety of biological functions related to chronic pain and inflammation. The main target is thought to be the peroxisome proliferator-activated receptor alpha (PPAR-α). PEA also has affinity to cannabinoid-like G-coupled receptors GPR55 and GPR119. PEA cannot strictly be considered a classic endocannabinoid because it lacks affinity for the cannabinoid receptors CB1 and CB2. However, the presence of PEA (and other structurally related N-acylethanolamines) have been know to enhance anandamide activity by a so called "entourage effect".

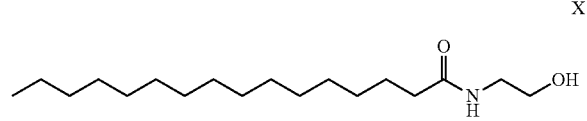 [SMILES: CCCCCCCCCCCCCCCC(=O)NCCO]

In certain embodiments, Applicant's keratolytic composition comprises no unsaturated fatty acids, no unsaturated fatty alcohols, or esters comprising unsaturated fatty acid moieties or unsaturated fatty alcohol moieties. In certain embodiments, Applicant's keratolytic composition comprises no compounds having one or more carbon-carbon double bonds.

Applicant has found that inclusion in his keratolytic emollient of unsaturated fatty acids, unsaturated fatty alcohols, or esters comprising unsaturated fatty acid moieties or unsaturated fatty alcohol moieties, results in decreased oxidative stability both prior to application to the skin, and after application to the skin. More generally, Applicant has found that inclusion in his keratolytic emollient of compounds having one or more carbon-carbon double bonds results in decreased oxidative stability both prior to application to the skin, and after application to the skin.

FIGS. 2A and 2B recite Formulations A, B, C, and D for different embodiments of Applicant's keratolytic emollient. The data recited in FIGS. 2A and 2B represent a weight percentage for each Compound recited.

FIGS. 3, 4, 5, 6, 7, 8, and 9, recite Formulations E, F, G, H, I, J, K, L, M, N, O, P, Q, R, S, T, U, V, W, X, Y, Z, AA, AB, AC, AD, AE, AF, AG, AH, AI, AJ, AK, AL, AM, AN, AO, AP, AQ, AR, AS, AT, AU, AV, AW, AX, AY, AZ, BA, BB, BC, BD, BE, BF, BG, BH, BI, BJ, BK, BL, BM, BN, BO, BP, BQ, BR, BS, BT, BU, BY, BW, BX, BY, BZ, CA, CB, CD, CE, CF, CG, CH, CI, CJ, CK, CL, CM, CN, CO, and CQ, for different embodiments of Applicant's keratolytic emollient. The data recited in FIGS. 3, 4, 5, 6, 7, 8, and 9, represent a weight percentages for each Compound recited. In each case, Formulations E, F, G, H, I, J, K, L, M, N, O, P, Q, R, S, T, U, V, W, X, Y, Z, AA, AB, AC, AD, AE, AF, AG, AH, AI, AJ, AK, AL, AM, AN, AO, AP, AQ, AR, AS, AT, AU, AV, AW, AX, AY, AZ, BA, BB, BC, BD, BE, BF, BG, BH, BI, BJ, BK, BL, BM, BN, BO, BP, BQ, BR, BS, BT, BU, BV, BW, BX, BY, BZ, CA, CB, CD, CE, CF, CG, CH, CI, CJ, CK, CL, CM, CN, CO, and CQ, further comprise 40 weight percent urea.

While the preferred embodiments of the present invention have been illustrated in detail, it should be apparent that modifications and adaptations to those embodiments may occur to one skilled in the art without departing from the scope of the present invention as set forth in the following claims.

I claim:

1. A keratolytic emollient, comprising:
   urea;
   mineral oil;
   paraffin wax; and
   N, N-2-ethanol-alginamide, wherein about 25 percent of the —COOH groups disposed in alginic acid have been converted to the amide of diethanol amine.

2. The keratolytic emollient of claim 1, wherein said keratolytic emollient does not comprise any compounds having one or more carbon-carbon double bonds.

3. The keratolytic emollient of claim 1, further comprising triethanolammonium alginate.

4. The keratolytic emollient of claim 3, wherein said keratolytic emollient does not comprise any compounds having one or more carbon-carbon double bonds.

5. The keratolytic emollient of claim 3, further comprising squalene.

6. The keratolytic emollient of claim 5, wherein said keratolytic emollient does not comprise any compounds having one or more carbon-carbon double bonds.

7. The keratolytic emollient of claim 5, further comprising cetyl palmitate.

8. The keratolytic emollient of claim 7, wherein said keratolytic emollient does not comprise any compounds having one or more carbon-carbon double bonds.

9. The keratolytic emollient of claim 7, further comprising ethylene glycol monostearate.

10. The keratolytic emollient of claim 9, wherein said keratolytic emollient does not comprise any compounds having one or more carbon-carbon double bonds.

11. The keratolytic emollient of claim 9, further comprising glycerin.

12. The keratolytic emollient of claim 11, wherein said keratolytic emollient does not comprise any compounds having one or more carbon-carbon double bonds.

13. The keratolytic emollient of claim 11, further comprising palmitoylethanolamide.

14. The keratolytic emollient of claim 13, wherein said keratolytic emollient does not comprise any compounds having one or more carbon-carbon double bonds.

15. The keratolytic emollient of claim 13, further comprising triethanolammonium alginate.

16. The keratolytic emollient of claim 15, wherein said keratolytic emollient does not comprise any compounds having one or more carbon-carbon double bonds.

17. The keratolytic emollient of claim 15, further comprising N, N-2-ethanol-guluronamide.

18. The keratolytic emollient of claims 17, wherein said keratolytic emollient does not comprise any compounds having one or more carbon-carbon double bonds.

19. The keratolytic emollient of claim 17, further comprising shea butter.

* * * * *